United States Patent [19]

Baum et al.

[11] 4,395,561
[45] Jul. 26, 1983

[54] SYNTHESIS OF 3-HYDROXYOXETANE

[75] Inventors: Kurt Baum, Pasadena; Vytautas Grakauskas, Arcadia, both of Calif.; Phillip T. Berkowitz, Woodbridge, Conn.

[73] Assignee: The United States of America as represented by the Secretary of the Navy, Washington, D.C.

[21] Appl. No.: 378,167

[22] Filed: May 14, 1982

[51] Int. Cl.³ ............................................. C07D 305/08
[52] U.S. Cl. ...................................... 549/510; 549/420
[58] Field of Search .......................................... 549/510

[56] References Cited

U.S. PATENT DOCUMENTS 4,009,182  2/1977  Ardis et al. ........................... 549/510

FOREIGN PATENT DOCUMENTS 321520  8/1972  U.S.S.R. ............................... 549/510

OTHER PUBLICATIONS

J. A. Wojtowicz et al., J. Org. Chem. (1973) vol. 38(11), pp. 2061–2066.
Bertin L. Emling et al., Jour. Am. Chem. Soc. (1941) vol. 63, pp. 1624–1625.
Louis E. Friedrich et al., J. Org. Chem. (1981), vol. 46(2), pp. 306–311.

Primary Examiner—Norma S. Milestone
Attorney, Agent, or Firm—R. F. Beers; K. E. Walden; R. D. Johnson

[57] ABSTRACT

A process for preparing 3-hydroxyoxetane comprising the following steps in order
(1) reacting a carboxylic acid of the formula $CH_3(CH_2)_nCOOH$ with epichlorohydrin in the presence of anhydrous ferric chloride to produce an ester of the formula

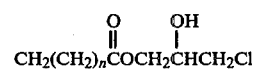

wherein n is an integer of from 0 to 3;
(2) protecting the secondary hydroxy group of the ester with a blocking group, Z, that is stable to bases; thus forming a blocked ester of the formula

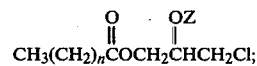

(3) hydrolyzing the blocked ester formed in step (2) with an aqueous base to remove the carboxylic acid and form a 3-hydroxyoxetane derivative of the formula

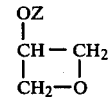

in which Z represents the blocking group;
(4) removing the blocking group from the 3-hydroxyoxetane derivative by heating it with an alcohol and an acid to form the product 3-hydroxyoxetane,

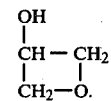

15 Claims, No Drawings

SYNTHESIS OF 3-HYDROXYOXETANE

BACKGROUND OF THE INVENTION

This invention relates to oxyoxetanes and more particularly to 3-hydroxyoxetane.

3-Hydroxyoxetane has been prepared previously by a sequence of reactions based on the chlorination of allyl alcohol with chlorine (Wojtowicz, J. A.; Polak, R. J.; Zaslowsky, J. A. *J. Org. Chem.* 1971, 38, 2061) or with t-butyl hypochlorite (Emling, B. L.; Vogt, R. R.; Hennion, C. G. *J. Am. Chem. Soc.* 1941, 63, 1624) to give a low yield of 2-allyloxy-3-chloropropanol. The 2-allyloxy-3-chloro-propanol was then treated with sodium hydroxide to give 3-allyloxyoxetane. The olefin portion of the 3-allyloxyoxetane was isomerized with potassium t-butoxide in dimethyl sulfoxide, and 3-hydroxyoxetane was then liberated by hydrolyzing off the olefin group using an acid catalyst in aqueous methanol. However, it would be desirable to find a more efficient method of producing 3-hydroxyoxetane.

SUMMARY OF THE INVENTION

Accordingly, it is an object of this invention to provide a new method of synthesizing 3-hydroxyoxetane.

Another object of this invention is to provide a more efficient method of producing 3-hydroxyoxetane.

A further object of this invention is to provide a simpler method of producing 3-hydroxyoxetane.

Yet another object of this invention is to reduce or eliminate the need for working up or purifying intermediate products in the production of 3-hydroxyoxetane.

These and other objects of this invention are achieved by providing:

A process for preparing 3-hydroxyoxetane comprising the following steps in order:

(1) reacting a carboxylic acid of the formula $CH_3(CH_2)_nCOOH$ with epichlorohydrin in the presence of anhydrous ferric chloride to produce an ester of the formula

$CH_3(CH_2)_nCOCH_2CHCH_2Cl$ (with O double bond on C, OH on middle CH)

wherein n is an integer of from 0 to 3;

(2) protecting the secondary hydroxy group of the ester with a blocking group, Z, that is stable to bases; thus forming a blocked ester of the formula

$CH_3(CH_2)_nCOCH_2CHCH_2Cl$ (with O double bond on C, OZ on middle CH);

(3) hydrolyzing the blocked ester formed in step (2) with an aqueous base to remove the carboxylic acid and form a 3-hydroxyoxetane derivative of the formula

in which Z represents the blocking group;

(4) removing the blocking group from the 3-hydroxyoxetane derivative by heating it with an alcohol and an acid to form the product 3-hydroxyoxetane,

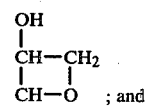
; and (5) isolating the product 3-hydroxyoxetane.

3-Hydroxyoxetane is useful as a component in propellants.

DETAILED DESCRIPTION OF THE PREFERRED EMBODIMENT

In the first step of the present process a carboxylic acid of the formula $CH_3COOH$, $CH_3CH_2COOH$, $CH_3CH_2CH_2COOH$, or $CH_3CH_2CH_2CH_2COOH$, is reacted with epichlorohydrin under anhydrous conditions in the presence of catalytic amounts of anhydrous ferric chloride to produce the corresponding 3-chloro-2-hydroxy-1-propyl ester;

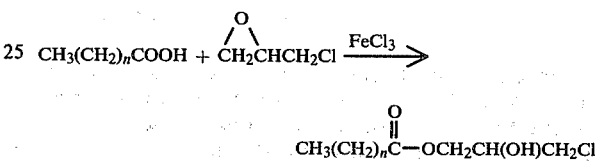

(wherein n as integer of from 0 to 3). Glacial acetic acid is the preferred carboxylic acid reactant because it is the least expensive.

Preferably, a trace amount of anhydrous $FeCl_3$ is used. This amount is sufficient to catalyze the reaction and at the same time eliminates the need for a special step to remove the catalyst.

Example 1, further illustrates the reaction conditions for this step. Note that the reaction is exothermic and therefore precautions such as slow addition of the carboxylic acid, constant stirring of the reaction mixture, and cooling are required during the initial stage of the reaction. After this initial stage, the reaction is preferably run at a temperature in the range of about 20° C. to about 100° C. as illustrated by Example 8; higher temperatures speed up the reaction.

After the excess carboxylic acid is removed by vacuum, the crude reaction product from step 1 may be used in the next step without first removing the traces of $FeCl_3$. It would appear that other Lewis acids would be suitable as the catalyst for this reaction. However, many of the Lewis acids catalyze the polymerization of epichlorohydrin and are therefore not suitable for this reaction.

The second step consists of blocking the secondary hydroxy in the reaction product of step 1.

Initially in this work, dihydropyran, a commonly used blocking reagent, was utilized. The reaction was catalyzed with pyridinium p-toluenesulfonate.

(IIA)
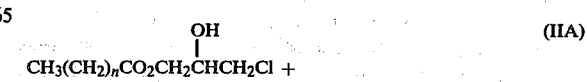

-continued

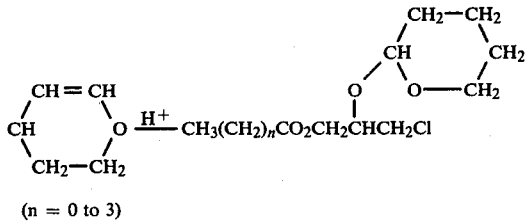

(n = 0 to 3)

Example 2 further illustrates this reaction. Subsequently it was found that ethyl vinyl ether, which is less costly than dihydropyran, gave similar results. Other alkyl vinyl ethers such as propyl vinyl ether, n-butyl vinyl ether, and isopentyl vinyl ether may also be used as the blocking agent.

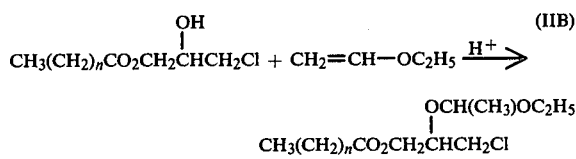

A trace amount of toluenesulfonic acid also catalyzes the reaction, again making it possible to use the crude reaction mixture as starting material for the next step. Example 3 further illustrates that reaction.

Heating the blocked esters (from IIA or IIB) with aqueous sodium hydroxide, potassium hydroxide, or a similar hydroxyl ion source results in the hydrolysis of the ester groups and then ring closure. In larger scale work this reaction is quite exothermic, but the reaction can be controlled by adding the ester slowly to hot aqueous sodium hydroxide, potassium hydroxide, or a similar aqueous strong hydroxyl ion source.

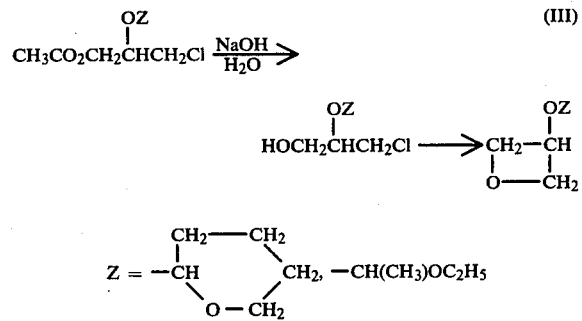

The blocking groups Z, were then removed by treating the materials with an alcohol and an acid catalyst. Initially, pyridinium p-toluenesulfonate was used as the catalyst, but in later work it was found that small amounts of p-toluenesulfonic acid functioned similarly.

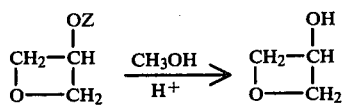

The 3-hydroxyoxetane can be isolated directly by distillation. Alternatively, it can be converted to the corresponding p-toluenesulfonate (tosylate), a solid that is readily isolated. The tosylate is more stable than the alcohol toward long term storage, and is useful for the preparation of other oxetane derivatives by displacement reactions. Example 12 illustrates the synthesis of the tosylate.

In the Experimental section below, examples 2, 3 and 4 describe exploratory experiments using dihydropyran as the blocking reagent. Example 5, 6 and 7 describe a similar set of experiments showing the feasibility of using ethyl vinyl ether as the blocking agent. Other alkyl vinyl ethers may be used as the blocking agents, but ethyl vinyl ether is preferred because of its low cost and its availability. Examples 8–12 were designed to convert this method into an industrial process. The use of solvents was eliminated where possible, and catalyst levels were minimized to eliminate work-up operations for intermediates.

The general nature of the invention having been set forth, the following examples are presented as specific illustrations thereof. It will be understood that the invention is not limited to these specific examples, but is susceptible to various modifications that will be recognized by one of ordinary skill in the art.

EXAMPLE 1

3-chloro-2-hydroxy-1-propyl acetate

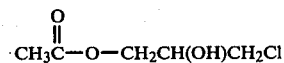

Epichlorohydrin (187 g, 2.0 mol) was added dropwise over a 75 minute period to a mechanically stirred suspension of 10.0 g (0.062 mol) of anhydrous ferric chloride in 138 mL (2.4 mol) of glacial acetic acid at 0°–10° C. After the addition was completed, the reaction mixture was stirred one hour and was allowed to stand at room temperature for two days. Anhydrous sodium acetate (5.1 g, 0.062 mol) was added and excess acetic acid was then removed in vacuo. The mixture was diluted with 200 mL of methylene chloride and filtered through Celite TM (i.e. diatomaceous earth). The solution was washed with 10% potassium carbonate and dried over potassium carbonate and sodium sulfate. Removal of the methylene chloride in vacuo gave 275 g of crude 3-chloro-2-hydroxy-1-propyl acetate, and an additional 9 g was recovered by extracting the potassium carbonate solution with methylene chloride (93% crude yield). This material was used without purification in the subsequent step. $^1$H NMR (CDCl$_3$) δ2.10 (s, 3H, —COCH$_3$); 3.80 (m, 6H, —CH$_2$CH(OH)CH$_2$—); IR (film) 3500 (—OH); 1735 cm$^{-1}$ (—COCH$_3$).

EXAMPLE 2

3-chloro-2-tetrahydropyranyloxy-1-propyl acetate

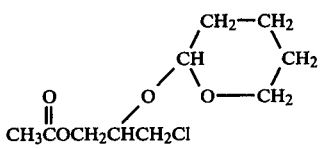

A solution of 271.9 g (1.78 moles) of 3-chloro-2-hydroxy-1-propyl acetate, 244 ml (2.67 moles) of freshly distilled dihydropyran, and 44.7 g (0.178 moles) of pyridinium p-toluenesulfonate in 1800 mL of methylene chloride was stirred at room temperature with cooling to control the reaction exotherm. After 22 hours the reaction mixture was washed with 500 mL of water and 250 mL of sodium chloride solution, and was dried over sodium sulfate. Solvent was removed and the residue was dried at 0.03 mm for 1.5 hours to give 473.3 g of crude 3-chloro-2-tetrahydropyranyloxy-1-propyl acetate: $^1$H NMR (CDCl$_3$) δ1.63 (br. s, 6 H, (CH$_2$)$_3$); 2.08 (s, 3H, CH$_3$CO); 3.5–4.3 (7H, CH$_2$CHCH$_2$); 4.73 (br. s, 1H, —O—CH); IR (neat, NaCl) 3000, 2910 (C—H); 1740 cm$^{-1}$ (—O—CO—CH$_3$).

EXAMPLE 3

3-tetrahydropyranyloxyoxetane

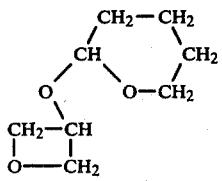

To 476 g of crude 3-chloro-2-tetrahydropyranyloxy-1-propyl acetate was added 216 g (5.4 moles) of sodium hydroxide in 500 mL of water. The reaction mixture was heated at reflux for 17 hours. The upper organic layer was separated and taken up in 350 mL of methylene chloride. The methylene chloride solution was dried over sodium sulfate and solvent was removed in vacuo to leave 320.9 g of 3-tetrahydropyranyloxyoxetane: $^1$H NMR (CDCl$_3$) δ1.63 (br. s, 6H, CH$_2$); 3.2–4.4 (m, 2H, —OCH$_2$); 4.47 (br. s, 1H, CH); 4.67 (br. s, 4H, O(CH$_2$)); 5.17 (br, s, 1H, O—CH); IR (CH$_2$Cl$_2$) 2970, 2910 (C—H); 980 cm$^{-1}$ (oxetane). Extraction of the aqueous layer with ether gave an additional 10.3 g for an overall crude yield of 331.2 g. 3-Tetrahydropyranyloxyoxetane distilled with some decomposition at 48°–65° (0.2 mm).

EXAMPLE 4

3-hydroxyoxetane

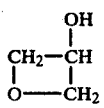

A solution of 205 g of crude 3-tetrahydropyranyloxetane and 11.3 g (0.045 moles) of pyridinium p-toluenesulfonate in 3 L of methanol was refluxed for 14 hours. The methanol was removed in vacuo and the residue was extracted with ether. The ether solution was filtered through sodium sulfate and the solvent was removed in vacuo. The residue was vacuum distilled to give 50.6 g of 3-hydroxyoxetane, bp 69°–75° C. (12 mm); (lit. bp 72–73 (9 mm); *J. Org. Chem.* (1971, 38, 2061). The overall yield of 3-hydroxyoxetane from 3-chloro-2-hydroxy-1-propyl acetate was 40.0%, and from epichlorohydrin, 37.1%.

The reaction was repeated using 805 g of crude 3-tetrahydropyranyl oxetane and gave a 46.7% yield of distilled 3-hydroxyoxetane, based on epichlorohydrin.

Examples 5, 6, and 7 illustrate the use of ethyl vinyl ether as the blocking reagent.

EXAMPLE 5

3-chloro-2-(1-ethoxyethoxy)-1-propyl acetate

A solution of 30.5 g (0.20 mol) of 3-chloro-2-hydroxy-1-propyl acetate (prepared in Example 1), 22 g (0.30 mol) of ethyl vinyl ether, and 7.5 g (0.030 mol) of pyridinium p-toluenesulfonate in 150 mL of methylene chloride was stirred at room temperature for 6 hours. The solution was then washed with 75 mL of water, dried and stripped of solvent in vacuo to give 44.0 g (98.0%) of 3-chloro-2-(1-ethoxyethoxy)-1-propyl acetate: $^1$H NMR (CDCl$_3$) δ1.05–1.37 (overlapping t and d, 6H, —CH$_2$CH$_3$ and —CHCH$_3$); 2.07 (s, 3H, —COCH); 3.53 and 4.12 (m. 7H, —CH$_2$CHCH$_2$ and —CH$_2$CH$_3$); 4.72 (q, J=4 Hz, 1H, —CHCH$_3$); IR (film) 1740 cm$^{-1}$ (—COCH$_3$). The unpurified product was used in the next step.

EXAMPLE 6

3-(1-ethoxyethoxy)oxetane

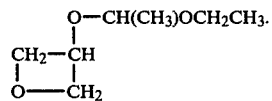

A mixture of 33.7 g (0.15 mol) of 3-chloro-2-(1-ethoxyethoxy) propyl acetate and 18 g (0.45 mol) of sodium hydroxide in 45 mL of water was heated at reflux for 21 hours. The reaction mixture was then cooled to room temperature and extracted first with 150 mL of 2:1 methylene chloride-ether and then with 100 mL of 1:1 methylene chloride-ether. The solution was dried and solvent was removed to give 19.0 g of crude 3-(1-ethoxyethoxy)oxetane: $^1$H NMR (CDCl$_3$) δ1.00–1.40 (overlapping t and d, 6H, —CH$_2$CH$_3$ and —CHCH$_3$); 3.52 (q, J=4 Hz, 2H, —CH$_2$CH$_3$), 4.60 (m, 6H,

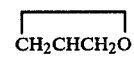

and —CHCH$_3$); IR (film) 980 cm$^1$ (oxetane).

EXAMPLE 7

3-hydroxyoxetane

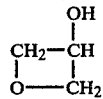

A solution of 15.0 g of crude 3-(1-ethoxyethoxy)oxetane and 0.58 g (2.3 mmol) of pyridinium p-toluenesulfonate in 75 ml of methanol was heated at reflux for 16 hours. The methanol was removed in vacuo and the residue was extracted with ether (50 mL and 10 mL). Removal of the ether in vacuo left 7.0 g of crude 3-hydroxyoxetane, which did not contain significant impurities on the basis of $^1$H NMR and gas chromotography. Vacuum distillation afforded 3.7 g of 3-hydroxyoxetane, bp 63°–68° C. (4.0 mm). The overall yield of distilled 3-hydroxyoxetane from epichlorohydrin was 39.4%.

EXAMPLE 8

3-chloro-2-hydroxy-1-propyl acetate

To a stirred solution of 1.5 g of anhydrous ferric chloride in 612 g (10.02 moles) of glacial acetic acid was added 925 g (10.0 moles) of epichlorohydrin at 20° C. over a period of 10 minutes. The reaction temperature increased to 28° C. The mixture was then heated at 65°–70° C. for 24 hours. The $^1$H NMR spectrum of the product was identical with that of Example 1. The material was used in the next step.

EXAMPLE 9

3-chloro-2-(1-ethoxyethoxy)-1-propyl acetate

To the crude acetate prepared in Example 8 was added 10 g of p-toluenesulfonic acid monohydrate and then dropwise, over a period of 2 hours, 815 g (11.3 moles) of ethyl vinyl ether. The reaction was midly exothermic and the temperature was maintained at 35°–37° C. by occasional cooling. After the addition was complete, the reaction mixture was heated at 35°–40° C. for 16 hours. The crude material was used in the subsequent step.

EXAMPLE 10

3-(1-ethoxyethoxy)oxetane

The crude 3-chloro-2-(1-ethoxyethoxy)-1-propyl acetate produced in Example 9 was added over a period of 1.5 hours to a stirred hot (105°) solution of 1.1 kg (27.5 moles) of sodium hydroxide in 1.1 L of water in a 5 L three-necked round-bottomed flask equipped with a mechanical stirrer, a reflux condenser, a dropping funnel, and a thermometer. The mixture was refluxed for an additional 4 hours period and then was allowed to cool to 25° C. The mixture was stirred with 1.5 L of water to dissolve inorganic salts and the phases were separated. The aqueous solution was extracted with 2 L of methylene chloride. Solvent was removed from the methylene chloride layer and the residual oil was combined with the above organic phase to give 1.2 kg of crude 3-(1-ethoxyethoxy) oxetane.

EXAMPLE 11

3-hydroxyoxetane

The above crude 3-(1-ethoxyethoxy)oxetane was diluted with 400 g of methanol and was cooled to 15°–18° C. To the stirred solution was added 10 g of p-toluenesulfonic acid hydrate. The reaction temperature increased over 5 minutes to 33°–4° C. and then decreased over a 30 minute period to 25° C. The mixture was stirred for an additional 45 minute period and then 5 g of solid sodium bicarbonate was added to neutralize the p-toluenesulfonic acid. Distillation gave 280 g of a colorless liquid, bp 45°–50° (0.3 mm), which was identified by $^1$H NMR as 3-hydroxyoxetane of 75–80% purity. This material is suitable for conversion to oxetyl tosylate without further purification, or pure 3-hydroxyoxetane can be isolated by fractionation. The overall yield based on epichlorohydrin is 30%.

EXAMPLE 12

3-oxetyl tosylate

The unpurified 3-hydroxyoxetane produced in Example 11 was used directly in the synthesis of its tosylate.

To a stirred suspension of 315 g of the material (containing 3.4 moles of 3hydroxyoxetane) and 743 g (3.9 moles) of technical grade p-toluenesulfonyl chloride in 600 mL of water, was added dropwise, over a period of 25 minutes, a solution of 218 g (5.45 moles) of sodium hydroxide in 225 mL of water. The reaction was exothermic and ice bath cooling was used to keep the reaction temperature below 70° C. When the exothermic reaction subsided (10 minutes), the cooling bath was removed and the reaction temperature was allowed to decrease to 40° C. over a 1 hour period. The product was isolated by filtration, washed with four 200 ml portions of warm (45°–55° C.) water, and air dried to give 730 g (94% yield) of 3-oxetyl tosylate, mp 86°–88° C.

Obviously numerous modifications and variations of the present invention are possible in light of the above teachings. It is therefore understood that within the scope of the appended claims the invention may be practiced otherwise than as specifically described herein.

What is claimed as new and desired to be secured by Letters Patent of the United States is:

1. A process for preparing 3-hydroxyoxetane comprising the following steps in order:
(1) reacting a carboxylic acid of the formula CH$_3$(CH$_2$)$_n$COOH with epichlorohydrin in the presence of a catalytic amount of anhydrous ferric chloride to produce an ester of the formula

wherein n is an integer of from 0 to 3;
(2) reacting the ester formed in step (1) with a blocking agent selected from the group consisting of
(a) dihydropyran,
(b) ethyl vinyl ether,
(c) propyl vinyl ether,
(d) n-butyl vinyl ether, and
(e) isopentyl vinyl ether
in the presence of a catalyst selected from the group consisting of pyridinium p-toluenesulfonate and toluenesulfonic acid to form a blocked ester of the formula

wherein n is an integer of from 0 to 3 and Z is selected from the group consisting of

 (a)

 (b)

 (c)

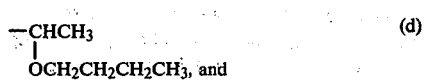 (d)

and

-continued $$-\underset{\underset{OCH(CH_2CH_3)_2}{|}}{CHCH_3}, \text{respectively;} \quad (e)$$

(3) hydrolyzing the blocked ester formed in step (2) with an aqueous base to remove the carboxylic acid and form a 3-hydroxyoxetane derivative of the formula $$\underset{\underset{CH_2-O}{|}}{\overset{OZ}{\underset{|}{CH-CH_2}}}$$

wherein Z is defined in step (2);

(4) removing the blocking group from the 3-hydroxyoxetane derivative by heating it with an alcohol and an acid to form the produce 3-hydroxyoxetane, $$\underset{\underset{CH_2-O;}{|}}{\overset{OH}{\underset{|}{CH-CH_2}}} \text{ and}$$

(5) isolating the product 3-hydroxyoxetane.

2. The process of claim 1 wherein the carboxylic acid used in step (1) is acetic acid and the ester produced is 3-chloro-2-hydroxyl-1-propyl acetate, $$CH_3\overset{O}{\overset{\|}{C}}OCH_2\overset{OH}{\underset{|}{C}}HCH_2Cl.$$

3. The process of claim 1 wherein the reaction temperature of step (1) is kept in the range of from about 20° C. to about 100° C.

4. The process of claim 1 wherein dihydropyran is used as the blocking agent in step (2).

5. The process of claim 4 wherein a trace amount of toluenesulfonic acid is used as the catalyst in step (2).

6. The process of claim 1 wherein the blocking agent used in step (2) is selected from the group consisting of ethyl vinyl ether, propyl vinyl ether, n-butyl vinyl ether, and isopentyl vinyl ether.

7. The process of claim 6 wherein the blocking agent used in step (2) is ethyl vinyl ether.

8. The process of claim 6 wherein a trace amount of toluenesulfonic acid is used as the catalyst in step (2).

9. The process of claim 1 wherein the based used in step (3) is NaOH.

10. The process of claim 1 wherein the base used in step (3) is KOH.

11. The process of claim 1 wherein the hydrolysis of step (3) is performed at reflux temperature.

12. The process of claim 1 wherein the alcohol used in step (4) is selected from the group consisting of methanol, ethanol, 1-propanol, 2-propanol, and mixtures thereof.

13. The process of claim 12 wherein the alcohol is methanol.

14. The process of claim 1 wherein the acid catalyst used in step (4) is toluenesulfonic acid.

15. The process of claim 1 wherein the acid catalyst used in step (4) is pyridinium p-toluenesulfonate.

* * * * *